(12) United States Patent
Flint

(10) Patent No.: US 10,744,349 B2
(45) Date of Patent: Aug. 18, 2020

(54) NAIL POLISH FORMULATION

(71) Applicant: Christina Flint, Chino, CA (US)

(72) Inventor: Christina Flint, Chino, CA (US)

( * ) Notice: Subject to any disclaimer, the term of this patent is extended or adjusted under 35 U.S.C. 154(b) by 0 days.

(21) Appl. No.: 15/016,127

(22) Filed: Feb. 4, 2016

(65) Prior Publication Data

US 2016/0220474 A1   Aug. 4, 2016

Related U.S. Application Data

(60) Provisional application No. 62/112,077, filed on Feb. 4, 2015.

(51) Int. Cl.
| | |
|---|---|
| *A61Q 3/02* | (2006.01) |
| *A61K 8/55* | (2006.01) |
| *A61K 8/35* | (2006.01) |
| *A61K 8/41* | (2006.01) |
| *A61K 8/73* | (2006.01) |
| *A61K 8/37* | (2006.01) |

(52) U.S. Cl.
CPC .................. *A61Q 3/02* (2013.01); *A61K 8/35* (2013.01); *A61K 8/375* (2013.01); *A61K 8/416* (2013.01); *A61K 8/55* (2013.01); *A61K 8/731* (2013.01); *A61K 2800/594* (2013.01); *A61K 2800/95* (2013.01)

(58) Field of Classification Search
CPC .......... A61K 2800/594; A61K 2800/95; A61K 8/35; A61K 8/375; A61K 8/416; A61K 8/55; A61K 8/731; A61Q 3/02
See application file for complete search history.

(56) References Cited

U.S. PATENT DOCUMENTS

2012/0118314 A1*   5/2012   Haile ................... A45D 34/045
                                                               132/200

* cited by examiner

*Primary Examiner* — Michael B. Pallay
(74) *Attorney, Agent, or Firm* — Donn K. Harris

(57) ABSTRACT

A formulation for a nail polish composition which is curable with UV light is provided. The composition can be applied in a single coating and does not include solvents such as tolualene, dibutyl phthalate, or formaldehyde. The coating once cured provides multi-coating results using only a single coating and can be covered with an optional gloss or other decorative top coating.

3 Claims, No Drawings

NAIL POLISH FORMULATION

This application is a nonprovisonal application of provisional application No. 62/112,077 filed on Feb. 4, 2015, and is incorporated herein by this reference.

BACKGROUND OF THE INVENTION

1. Field of the Invention

The present invention relates generally to coatings or polishes applied to the fingernails and toenails of individuals. More particularly, it relates to a formulation of nail polish composition, yielding a UV-cured polish which does not contain solvents such as Tolualene, Dibutyl Phthalate, or Formaldehyde, and provides multi-coating results using only one coating which can be covered with an optional gloss.

2. Prior Art

In more modern times, it has become hygienic and fashionable to apply coatings of material to the fingernails and toenails of individuals. Such coatings may be a single layer of clear or transparent material, which cures to seal and strengthen the underlying fingernails or toenails.

A widely employed mode of such nail coatings, employs a film-forming polymer dissolved in a volatile organic solvent that can be applied to the human fingernails or toenails to decorate and protect the nail plates. The solution dries to a film covering the nails dries by evaporation of the volatile solvent in a curing process that generally produces a hard, durable finish on the nails to which it is applied.

In more modern times in the U.S. and many foreign countries, the applications of such liquid coatings to nails has become more popular for the decorative aspects as well as the hygienic and nail care aspects of such coatings.

In more recent times, the application of coatings to fingernails and toenails has come to include liquid coatings which may be cured quickly using Ultraviolet Light, or (UV) cured coating. Such coatings cure more quickly than those requiring evaporation of conventional solvents noted above.

In use, UV cured coatings are applied to the nail of choice, to cover the desired areas. With the liquid covering all or the portions of the nail of choice, the nail with the coating thereon, is positioned to receive UV light for a short time.

The UV light so communicated causes a curing and hardening of the liquid material forming the coating, and it hardens to an adhered coating on the fingernail or toenail. Conventionally, at least three applications of the liquid coating material are applied to the nails of the person. For each such applied layer, the nail must be exposed to the UV light source. Thus, for each nail on each finger or toe, once covered by the uncured liquid, that coating must be exposed to UV in the curing process. Such can be time consuming when where each subsequent layer positioned on a prior layer on a nail, must be exposed to UV light for a determined duration of time.

Conventionally, a first layer is placed on each nail as a primer coat. This primer coat provides a secure interface engagement between the underlying nail surface and the coating material deposited thereon once exposed to UV light in a first exposure. The second coating is then subsequently placed on the cured primer coating, and conventionally will have pigments and other suspended solids in the formed UV-curable carrier liquid used in the coating. This second coating on each nail must be then exposed to the UV light source for the prescribed duration of time to cure.

Once both the primer coating and the second coating are applied and cured using exposure to UV light, conventionally a top coating is applied to the underlying primer and first coats. This top coat may be protective in that it resists abrasion and the like, and can impart a desired sheen to the underlying cured coatings, to thereby protect the ornamental aspects of the second coat underneath. Once applied, this third coating must then be cured by exposure to the UV light source for the required duration of time.

As can be discerned, this multiple coating of each of the plurality of fingernails or toenails, and the required subsequent UV curing of each layer placed on each finger or toe, is extremely time consuming. Further, a number of problems arise with conventional nail coatings which occur in this process.

A first problem arises when, in order to save time, many practitioners will sequentially coat all the nails on a single hand or foot with the liquid material. The practitioner will then expose all of the nails to a UV light source to cure. However, exposing all of the sequentially applied coatings to the same UV light source at the same time, frequently results in uneven coatings on each finger or toe occur. This occurs because the earlier coated nails have the uncured coating thereon must wait, while the subsequent toes or fingers of the hand or foot are then coated.

However, these earlier coated nails frequently suffer shrinkage while subsequent nails are being coated because volatile solvents contained in the previously applied coatings evaporate and begin to cure or dry, prior to exposure to UV Light. This shrinkage can have significant effects on the overall aesthetic outcome of the coatings, as well as the physical durability which will vary by each nail, since the applied coating has shrunk differently on each before the UV curing. Further, the later exposure of subsequent coating layers to UV light, also exposes the underlying layers to a portion of that UV light which is communicated through the overlying layer. This can have detrimental effects on the underlying layers from excess exposure or over curing.

Another problem inherent to the conventional coating system for nails is the requirement for multiple coatings. These multiple coatings are applied for better protection and the enhanced appearance of the nails, and are applied to adhere over the underlying primer coat. Further, the primer coat is also frequently employed to "fill" depressions which occur in the nails to provide a smoother appearance to the final outcome for the overlaying coatings. Consequently, multiple coatings using a primer and overcoats are preferred, in this time consuming process because at present there are no alternatives available.

Additionally, problematic in the two or three layer coating system, is that the mid coating and/or the top coating can suffer from uneven drying, shrinkage, which presents a problem to the practitioner applying the coatings in repairing a mistake or defect on an overlying coating without affecting the underlying coatings. Further, any such uneven drying or shrinkage in overlying coatings can cause an overly brittle top coat, which chips on impact.

As such, there exists an unmet need, for a nail coating liquid which is UV-curable, and which does not contain volatile solvents which can cause curing of the coating prior to communication of UV light thereto. Such a coating composition should be formulated to allow for a reduction of the number of coatings used to one or optionally two coatings if a sheen or other coat is desired. Such a formulation will not only save both the customer and vendor time, and lead to price reductions for the customer, such a UV curable liquid coating for nails should also provide a remedy to the shortcomings of the current art noted.

To that end, such a UV curable coating system should allow for one coat which is formulated to achieve a strong engagement directly to an underlying nail surface and should have spreading properties which provide it an affinity to fill depressions in the nail surface. Such a coating even when filling depressions as noted, must still provide a smooth opposing surface on the top of the coating once cured. Still further such a coating material once cured, should be sufficiently blastomeric to resist chipping and fracture on impact, but still sufficiently hard to protect the coating under the exposed surface.

The forgoing examples of related art and limitations related therewith are intended to be illustrative and not exclusive, and they do not imply any limitations on the disclosed UV curable nail coating invention and method described and claimed herein. Various limitations of the related art are already or will become apparent to those skilled in the art upon a reading and understanding of the specification below and the accompanying drawings.

SUMMARY OF THE INVENTION

The coating formulation and method herein disclosed and described provides a solution to the shortcomings in prior art of UV curable nail coatings used for hygienic as well as cosmetic purposes. The formulation forming the nail composition herein is employable in a single base coat with excellent results, once cured by a UV light source. Optionally, a top coat can be applied in a 2-step process to enhance the sheen or other ornamental and protective aspects of the base coat.

Thus, the formulation yields in a single coating, excellent adhesion and cured appearance such that no basecoat, bonder, or primer is required for application to the nails, to attain adhesion to the nail bed, film decal or acrylic nails.

As noted, while one coat provides excellent results when cured, a clear or colored topcoat may be applied for sheen or gloss. Further, the base coat and the top coat may include pigments, pearls and glitters for a visual effect.

The surface of the cured gel polish is susceptible to UV, solvent, waterborne acrylic coatings sometimes referred to nail art. The formulation for the coating system herein disclosed contains no volatile solvents which cause shrinking prior to UV curing, and provide a final cured coating to a fingernail or toenails which has superior flexible elongation when cured. This renders the cured coating to one especially well-adapted to prevent cracking and chipping or breakage caused by elongation from nail growth which inherently stretches any applied cure coating thereon.

Further the formulation herein disclosed provides an improved coating for nails which has a high gloss, no shrinkage before or during curing. Further, the formulation is adapted to cure under UV light from conventional bulbs or UV projecting LED lights.

Once applied in a single or dual coating, experimentation has shown the resultant UV cured coating will last up to three weeks of wear without breakage from elongation caused by growing nails, or chips and cracks from impacts, or other perils of cured nail polish. Additionally, while the UV liquid herein contains no solvent which as noted causes shrinkage prior to UV curing, it provides a cured coating which is sufficiently hard to resist chipping, which is easily removable, and which is very resistant to many chemicals and soaps the user might encounter. Still further, the formulation for the UV curable coating contains no Tolualene, Dibutyl Phthalate, or Formaldehyde which are hazardous to both customer and professional applicator, but used in conventional nail coating formulations.

With respect to the above description, before explaining at least one preferred embodiment of the herein UV curable nail coating formulation and system and method in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing other nail coatings, methods and systems for carrying out the several purposes of the present disclosed device and method. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of the disclosed nail coating material and system herein to provide an easier to apply and more durable UV curable coating for nails.

These and other objects features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

DETAILED DESCRIPTION OF THE PREFERRED EMBODIMENTS OF THE INVENTION

In this description, the directional prepositions of up, upwardly, down, downwardly, front, back, top, upper, bottom, lower, left, right and other such terms refer to the device as it is oriented and appears in the drawings and are used for convenience only and they are not intended to be limiting or to imply that the device has to be used or positioned in any particular orientation.

Now referring to the formulations herein employed for nail coatings which have no solvents and which are UV-curable, the coating formulations may be employed in one basecoat with excellent protective and visual results. Optionally, a second topcoat can be applied over the singe base coat. In either mode, the material is easily cured to a final coating surface using conventional UV or LED type UV lamps. So cured, the formulation results in a significantly improved UV gel polish system over the prior art.

As noted it can be employed in a one step system of gel polish with no basecoat, bonder, or primer required and yet still attain equal or improved adhesion to the nail bed as conventional three step systems using a primer layer. A second coating may be applied to the first shine, sheen, or other ornamental or protective aspects. The formulation applied in either a single coat or with a two-coat process, provides excellent adhesion to a film decal or acrylic nails.

If a two-step process is employed, a topcoat is optionally applicable over the single underlying coat for additional gloss or sheen or other ornamental aspects. Further, the single coat or the top coat or both may also contain pigments, pearls and glitter for visual effect, although such is optional. The resulting surface of the cured gel polish is susceptible to UV, solvent, waterborne acrylic coatings which are sometimes employed and referred to nail art.

The formulation herein disclosed provides for a coating with flexible elongation to prevent cracking or breaking on the nail during nail growth which causes stretching of an applied coating. As noted, it cures to a high gloss with virtually no shrinkage prior to communication of UV light due to the elimination of solvents. It further has virtually no shrinkage once cured under UV and LED light. The cured coating will last up to three weeks of wear without breakage and contains no solvents. As noted, it cures sufficiently hard to prevent chipping, but is still easily removable, resistant to many chemicals and soaps, and contains no Tolualene, Dibutyl Phthalate, or Formaldehyde.

The preferred composition of liquid coating material includes by percentage by weight, a mixture of oligomers, monomers, accelerators, and adhesives each of which is a percentage of the total formulation, however it should be noted that any one or all of each group can be employed to yield the noted percentage. The components yielding the composition herein in all modes, are mixed to yield the liquid uv-curable composition in the conventional fashion. All particularly preferred formulations provided herein, have been shown in experimentation, without the inclusion of solvents, to provide the coverage and curing to allow for a single coating layer, and the elongation once cured to accommodate nail growth for two to three weeks and not crack or peel.

It should be noted that the CAS Registry numbers and one of many possible suppliers for most components of the formulation yielding the composition herein, are included to provide clarity and identify each individual component. Further, by "substantially" is meant the stated weight percentage of mixture components or groups of the total mixture noted, which has been found in experimentation to provide an exceptional coating material, or the stated percentage stated plus or minus two percent variance.

The preferred formulation of the composition, includes a first mixture component which is substantially 45% by weight of the total composition, consisting of one or more oligomers, from a group of oligomers including Di-HEMA Trimethylhexyl Dicarbamate-low molecular Weight, available from Angene International Limited, U.K. (CAS Registry Number 72869-86-4); Di-HEMA Trimethylhexyl Dicarbamate-high molecular weight, available from Angene International Limited, U.K. (CAS Registry Number 72869-86-4); and, UDMA-TD10, a.k.a., METHACRYLIC ACID2-[[[[(5-ISOCYANATO-1,3,3-TRIMETHYLCYCLOHEXYL) METHYL]AMINO]CARBONYL]OXY]ETHYL ESTER, (CAS Registry Number 73597-26-9) (available from Angene International Limited, UK)

Di-HEMA Trimethylhexyl Dicarbamate low molecular weight (CAS Registry Number 72869-86-4), is a preferable oligomer, as under UV light it cures to form a hard, glassy surface that is low in color and is considered bisphenol A free. Di-HEMA Trimethylhexyl Dicarbamate-high molecular weight, is another preferred included oligomer as it results in lower polymerization shrinkage when cured due to this high molecular weight. Mixed with low molecular weight Di-HEMA Trimethylhexyl Dicarbamate in the noted favored proportions, it yields a formulation for the coating material which upon curing will have a high glossy surface, low material color to effect added colorizers, and little or no shrinkage.

The preferred formulation includes a second mixture component, which is substantially 25.7%% by weight of the total composition, consisting of one or more monomers, from a group of monomers including, 2 Hydroxypropyl Methacrylate (CAS Registry Number 27813-02-1; 2 Hydroxy Ethyl Methacrylate (CAS Registry Number 868-77-9);PMGDM a.k.a. Pyromellitic glycerol dimethacrylate (CAS Registry Number 148019-46-9).

These are preferred included monomers because 2 Hydroxypropyl Methacrylate (CAS Registry Number 27813-02-1), is considered to have less allergic reaction potential than other methacrylates which is important in coatings to the body, and, 2 Hydroxy Ethyl Methacrylate (CAS Registry Number 868-77-9), has adhesive qualities and multiple applications of other hydroxymethyl methacrylates, along with additional stability. Further, PMGDM a.k.a. Pyromellitic glycerol dimethacrylate (CAS Registry Number 148019-46-9), when included, has been found to enhance bonding of the mixed coating composition of the composition herein, because it includes four methacrylate groups and two carboxylic acid groups to enhance bonding to various substrates.

The preferred composition includes a third mixture component, which is substantially 19% by weight of the total composition, consisting of one or more cure accelerators, from a group of cure accelerators, including, 2,4,6-Trimethyl-Benzoyl-Diphenyl,(CAS Registry Number 75980-60-8); and 1-Hydroxy Cyclohexexyl Phenyl Keytone (CAS Registry Number 947-19-3); and 2 Hydroxy-2-methylpropiophenone (CAS Registry Number 7473-98-5).

The preferred composition includes a fourth mixture component, which is substantially 5.5% by weight of the total composition, consisting of one or more adhesion enhancers, from a group of adhesion enhancers, including, Silicone acrylate polyether, from Siltech Industries, and Triethylene Glycol Dimethacrylate (CAS Number 109-16-0)

The preferred composition includes a fifth mixture component, which is substantially 1.8% by weight of the total composition, consisting of one or more spread enhancers, to enhance liquid spread, from a group of spread enhancers, including Alkyl Quaternary Ammonium Clay, and Treated Silica (CAS Number 68611-44-9). These components when included have shown to enhance the spread of the liquid formulation and filling between nail ridges, prior to UV curing.

Additionally included in the preferred composition is an antioxidant in the form of Butylated Hydroxy Toluene (CAS Number 128-37-0) at a ratio of substantially 1% in weight of the total composition.

Finally, a resin in the form of Cellulose Acetate Butyrate, (CAS Number 9004-36-8) is included into the formulation at a ration of substantially 2% by weight of the total weight of the composition.

As noted the components of the composition herein are mixed in a conventional fashion for such UV-curable nail polish to yield the liquid coating material which is applicable to the nails of users.

Another particularly preferred mode of the formulation above, includes the noted mixture components of the composition in the following percentages by weight of the total compositon:

Oligomers substantially 45% by weight of the total composition, including:
  Di_HEMA Trimethylhexyl Dicarbamate-low molecular wt.
    Between 5% and 25%
  Di_HEMA Trimethylhexyl Dicarbamate-high molecular wt.
    Between 5% and 25%
  IPUDMA-TD10 UDMA-TD10, a.k.a., METHACRYLIC ACID2-[[[[(5-ISOCYANATO-1,3,3-TRIMETHYL-CYCLOHEXYL) METHYL]AMINO]CARBONYL]OXY]ETHYL ESTER, Between 5% and 25%
Monomers substantially 25.7% by weight of the total compositon:
  Hydroxypropyl Methacrylate, between 5% and 25.7%
  2 Hydroxy Ethyl Methacrylate, between 3% and 25.7%
  PMGDM a.k.a. Pyromellitic glycerol dimethacrylate between 0.1% and 25.7%
Cure Accelerators substantially 19% by weight of the total composition:
  TrimethylBenzoil Diphenyl Phosphine Oxide, Between 1% and 19%
  Hydroxy Cyclohexexyl Phenyl Keytone, Between 1% and 19%
  2 Hydroxy-2-methylpropiophenone, Between 1% and 19%
Adhesion Enhancers substantially 5.5% by weight of the total composition:
  Silicone polyether acrylate 0.5%
  Triethylene Glycol Dimethacrylate 5%
Fluid Spread Enhancers substantially 1.8% by weight of the total composition:
  Alkyl Quaternary Ammonium Clay 0.8%
  Treated Silica 1%
An Antioxidant substantially 1% by weight of the total compositon:
  Butylated Hydroxy Toluene 1%
A Resin substantially 2% by weight of the total composition, including:
  Cellulose Acetate Butyrate 2%

Still further, through experimentation, another particularly preferred combination of components of the formulation which has been found to provide exceptional coverage of nails, as well as a life span with minimal chipping and cracking, is a formulation including the following mixture components of the total composition:

Oligomers substantially 45% by weight, consisting of
  Di_HEMA Trimethylhexyl Dicarbamate-low molecular wt. 15%
  Di_HEMA Trimethylhexyl Dicarbamate-high molecular wt. 15%
  IPUDMA-TD10 UDMA-TD10, a.k.a., METHACRYLIC ACID2-[[[[(5-ISOCYANATO-1,3,3-TRIMETHYL-CYCLOHEXYL) METHYL]AMINO]CARBONYL]OXY]ETHYL ESTER, 15%
Monomers substantially 25.7% by weight consisting of:
  Hydroxypropyl Methacrylate 15%
  2 Hydroxy Ethyl Methacrylate 10.2%
  PMGDM a.k.a. Pyromellitic glycerol dimethacrylate 0.5%
Cure Accelerators substantially 19% by weight, consisting of:
  TrimethylBenzoil Diphenyl Phosphine Oxide 5%
  Hydroxy Cyclohexexyl Phenyl Keytone 4%
  2 Hydroxy-2-methylpropiophenone 10%
Adhesion Enhancers substantially 5.5% by weight, including:
  Silicone polyether acrylate 0.5%
  Triethylene Glycol Dimethacrylate 5%
Fluid Spread Enhancers substantially 1.8% by weight, including:
  Alkyl Quaternary Ammonium Clay 0.8%
  Treated Silica 1%
An Antioxidant substantially 1% by weight, consisting of
  Butylated Hydroxy Toluene 1%
A Resin substantially 2% by weight, consisting of
  Cellulose Acetate Butyrate 2%

As noted, from the above groups another member of the noted group can be substituted for one or all of the other members of the group. Further, as noted, particularly preferred in all modes of the formulation, is the inclusion of the Treated Silica which has been found to particularly improve the even spreading of the liquid for a smooth exposed surface over nail depressions and to maintain a smooth top surface prior to and after curing.

It is additionally noted and anticipated that although the UV curable mixture useable for a single or two coats on nails is shown in its most simple form, various components and aspects of the mixture as noted may be modified when forming the mixture herein such as the noted substitution of one or all components of one noted group for others therein. As such those skilled in the art will appreciate the descriptions and depictions set forth in this disclosure or merely meant to portray examples of preferred modes within the overall scope and intent of the invention, and are not to be considered limiting in any manner.

While all of the fundamental characteristics and features of the improved UV nail coating and method of employment have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A nail polish composition, comprising:
a first mixture component which is substantially 45% by weight of the total composition, consisting of one or more oligomers, from a group of oligomers consisting of: Di-HEMA Trimethylhexyl Dicarbamate, and, Methacrylic Acid2-[[[[(5-Isocyanato-1,3,3-Trimethylcyclohexyl) Methyl]Amino]Carbonyl]Oxy]Ethyl Ester;
a second mixture component, which is substantially 25.7% by weight of the total composition, consisting of one or more monomers, from a group of monomers consisting of: 2 Hydroxypropyl Methacrylate, 2 Hydroxy Ethyl Methacrylate, and Pyromellitic glycerol dimethacrylate;

a third mixture component, which is substantially 19% by weight of the total composition, consisting of one or more cure accelerators, from a group of cure accelerators, consisting of: 2,4,6-Trimethyl-Benzoyl-Diphenyl phosphine oxide, 1-Hydroxy Cyclohexexyl Phenyl Keytone, and 2 Hydroxy-2-methylpropiophenone;

a fourth mixture component, which is substantially 5.5% by weight of the total composition, consisting of one or more adhesion enhancers, from a group of adhesion enhancers, consisting of: Silicone acrylate polyether, and Triethylene Glycol Dimethacrylate;

a fifth mixture component, which is substantially 1.8% by weight of the total composition, consisting of one or more fluid spread enhancers, from a group of spread enhancers, consisting of: Alkyl Quaternary Ammonium Clay, and Treated Silica;

an antioxidant comprising Butylated Hydroxy Toluene at a concentration of substantially 1% by weight of the total composition; and a resin comprising Cellulose Acetate Butyrate, at a concentration of substantially 2% by weight.

2. The nail composition of claim 1 wherein

Said first mixture component includes as a weight of the total composition:

said Di_HEMA Trimethylhexyl Dicarbamate Between 5% and 40%;

said METHACRYLIC ACID2-[[[[(5-ISOCYANATO-1,3, 3-TRIMETHYLCYCLOHEXYL) METHYL] AMINO]CARBONYL]OXY]ETHYL ESTER, Between 5% and 25%;

said second mixture component includes as a weight of the total composition:

said Hydroxypropyl Methacrylate between 5% and 25.7% said 2 Hydroxy Ethyl Methacrylate between 3% and 25.7% said Pyromellitic glycerol dimethacrylate between 0.1% and 25.7%;

said third mixture component includes as a weight of the total composition:

said TrimethylBenzoil Diphenyl Phosphine Oxide between 1% and 19%;

said Hydroxy Cyclohexexyl Phenyl Keytone between 1% and 19%;

said 2 Hydroxy-2-methylpropiophenone between 1% and 19%;

said fourth mixture component includes as a weight of the total composition:

said Silicone polyether acrylate 0.5%;

said Triethylene Glycol Dimethacrylate 5%; and said fifth mixture component includes as a weight of the total composition:

said Alkyl Quaternary Ammonium Clay 0.8% said Treated Silica 1%.

3. A nail polish composition, comprising:

oligomers by weight, of the composition, comprising:
Di_HEMA Trimethylhexyl Dicarbamate 30%;
METHACRYLIC ACID2-[[[[(5-ISOCYANATO-1,3, 3-TRIMETHYLCYCLOHEXYL) METHYL] AMINO]CARBONYL]OXY]ETHYL ESTER 15%;

monomers by weight of the total composition, comprising:
Hydroxypropyl Methacrylate 15%;
2 Hydroxy Ethyl Methacrylate 10.2%;
Pyromellitic glycerol dimethacrylate 0.5%;

cure Accelerators by weight, of the composition, comprising:
TrimethylBenzoil Diphenyl Phosphine Oxide 5%;
Hydroxy Cyclohexexyl Phenyl Keytone 4%;
2 Hydroxy-2-methylpropiophenone 10%;

adhesion enhancers by weight of the total composition, comprising:
Silicone polyether acrylate 0.5%
Triethylene Glycol Dimethacrylate 5% fluid spread enhancers by weight of the total compositon comprising:
Alkyl Quaternary Ammonium Clay 0.8%;
Treated Silica 1%;

Butylated Hydroxy Toluene 1% by weight of the total compositon; and cellulose acetate butyrate 2% by weight of the total compositon.

* * * * *